United States Patent [19]

Burk et al.

[11] Patent Number: 5,416,106
[45] Date of Patent: May 16, 1995

[54] 7-[CARBOXYALKYL OR ALKENYL]-6-[ALKYL OR ALKENYL]3-OXO-2,4-DIOXOBICYCLO-[3.2.1] OCTANE AND DERIVATIVES THEREOF

[75] Inventors: Robert M. Burk, Laguna Beach; Achim H. Krauss, Irvine; David F. Woodward, El Toro, all of Calif.

[73] Assignee: Allergan, Inc., Irvine, Calif.

[21] Appl. No.: 174,534

[22] Filed: Dec. 28, 1993

[51] Int. Cl.⁶ .................. A61K 31/335; C07D 493/08
[52] U.S. Cl. ..................................... 514/450; 549/229
[58] Field of Search .......................... 514/450; 549/229

[56] References Cited

U.S. PATENT DOCUMENTS 4,599,353 7/1986 Bito .
4,994,274 2/1991 Chan et al. .
5,034,413 7/1991 Chan et al. .

FOREIGN PATENT DOCUMENTS 0364417 4/1990 European Pat. Off. .

OTHER PUBLICATIONS

Starr. M. S., "Further Studies on the Effect of Prostalgnadin on Intraocular Pressure in the Rabbit", *Exp. Eye Research,* (1971), 11, pp. 170–177.
Bito, L. Z., "Prostaglandins, Other Eicosanoids, and Their Derivatives as Potential Antiglaucoma Agents," *Applied Pharmacology in the Medical Treatment of Glaucomas* Drance, S. M. and Neufeld, A. H. eds., New York, Grune & Stratton, (1984), pp. 477–505.
Nilsson, et al., "PGF$_{2\alpha}$ Increases Uveoscleral Outflow", *Invest. Ophthalmol. Vis. Sci.* (suppl), 284, (1987).
Siebold, et al., "Esterified prostaglandin shows 'potent' promise", *Prodrug* 5 3, (1989).
Bito, L. Z., "Prostaglandins, Old Concepts and New Perspectives", *Arch. Ophthalmol.* 105, 1036, (1987).
Coleman, R. A., et al., Comparison of the Actions of U-46619, A Prostaglandin H2-Analogue, with Those of Prostaglandin H2 and Thromboxane A2 on some isolated *Br. J. Pharmacol.* 73:773–778 (1981).
Burk et al., Tetrahedron Letters (1993), 34(3), 395–8.

*Primary Examiner*—Johann Richter
*Assistant Examiner*—John Peabody
*Attorney, Agent, or Firm*—Robert J. Baran; Martin A. Voet; Howard R. Lambert

[57] ABSTRACT

The present invention relates to 7-[carboxyalkyl or alkenyl]-6-[alkyl or alkenyl]-3-oxo-2,4-dioxobicyclo[3.2.1] octanes and derivatives thereof. In particular, hydroxyl, nitro, amino, amido, azido, oxime, thiol, ether and thiol ether derivatives of said carboxy group are contemplated. In particular, 7-[6-carboxy-2-hexenyl]-6-[3-hydroxy-1-octenyl] of 3-oxo-2,4-dioxobicyclo-[3.2.1] octane and derivatives thereof are disclosed. These compounds are useful as ocular hypotensives and as (a) thromboxane mimetics for the prevention of hemorrhaging as follows:, during surgery; tooth extraction; hemorrhaging associated with gastro-intestinal diseases and conditions such as hemorrhoids, inflammatory bowel diseases and gastric and peptic ulcers; as a result of stroke; as a complication in retinal diseases resulting in impaired vision and associated with menstruation, childbirth and uterine dysfunction and (b) selective vasoconstrictors for treating systemic hypotension, e.g. in restoring normal blood pressure in hemorrhagic, anaphylactic, or septic shock victims; to provide local anti-inflammatory effects in the eye, skin and nose; to limit plasma exudation in burns, etc. and optimizing blood born delivery of drugs and diagnostics in encapsulating vehicles.

6 Claims, No Drawings

7-[CARBOXYALKYL OR ALKENYL]-6-[ALKYL OR ALKENYL]3-OXO-2,4-DIOXOBICYCLO-[3.2.1] OCTANE AND DERIVATIVES THEREOF

FIELD OF THE INVENTION

The present invention relates to 7-[carboxyalkyl or alkenyl]-6-[alkyl or alkenyl]-3-oxo-2,4-dioxobicyclo[3.2.1] octanes and derivatives thereof. In particular, hydroxyl, nitro, amino, amido, azido, oxime, thiol, ether and thiol ether derivatives of said carboxy group are contemplated. In particular, 7-[6-carboxy-2-hexenyl]-6-[3-hydroxy-1-octenyl] of 3-oxo-2,4-dioxobicyclo-[3.2.1] octane and derivatives thereof are disclosed. These compounds are useful as ocular hypotensives and as (a) thromboxane mimetics for the prevention of hemorrhaging as follows:, during surgery; tooth extraction; hemorrhaging associated with gastro-intestinal diseases and conditions such as hemorrhoids, inflammatory bowel diseases and gastric and peptic ulcers; as a result of stroke; as a complication in retinal diseases resulting in impaired vision and associated with menstruation, childbirth and uterine dysfunction and (b) selective vasoconstrictors for treating systemic hypotension, e.g. in restoring normal blood pressure in hemorrhagic, anaphylactic, or septic shock victims; to provide local anti-inflammatory effects in the eye, skin and nose; to limit plasma exudation in burns, etc. and optimizing blood born delivery of drugs and diagnostics in encapsulating vehicles.

BACKGROUND OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical $\beta$-adrenoreceptor antagonists have traditionally been the drugs of choice for treating glaucoma.

Prostaglandins were earlier regarded as potent ocular hypertensives; however, evidence accumulated in the last two decades shows that some prostaglandins are highly effective ocular hypotensive agents and are ideally suited for the long-term medical management of glaucoma. (See, for example, Starr, M.S. *Exp, Eye Res.* 1971, 11, pp. 170-177; Bito, L. Z. *Biological Protection with Prostaglandins* Cohen, M. M., ed., Boca Raton, Fla, CRC Press Inc., 1985, pp. 231-252; and Bito, L. Z., *Applied Pharmacology in the Medical Treatment Of Glaucomas* Drance, S. M. and Neufeld, A. H. eds., New York, Grune & Stratton, 1984, pp. 477-505). Such prostaglandins include $PGF_{2\alpha}$, $PGE_{1\alpha}$, $PGE_2$, and certain lipid-soluble esters, such as $C_1$ to $C_5$ alkyl esters, e.g. 1-isopropyl ester, of such compounds.

In the U.S. Pat. No. 4,599,353 certain prostaglandins, in particular $PGE_2$ and $PGF_{2\alpha}$ and the $C_1$ to $C_5$ alkyl esters of the latter compound, were reported to possess ocular hypotensive activity and were recommended for use in glaucoma management.

Although the precise mechanism is not yet known, recent experimental results indicate that the prostaglandin-induced reduction in intraocular pressure results from increased uveoscleral outflow [Nilsson et al., *Invest, Ophthalmol. Vis. Sci,* 28(suppl), 284 (1987)].

The isopropyl ester of $PGF_{2\alpha}$ has been shown to have significantly greater hypotensive potency than the parent compound, which was attributed to its more effective penetration through the cornea. In 1987 this compound was described as "the most potent ocular hypotensive agent ever reported." [See, for example, Bito, L. Z., *Arch. Ophthalmol.* 105, 1036 (1987), and Sicbold et al., *Prodrug* 5, 3 (1989)].

Whereas prostaglandins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g. its 1-isopropyl ester, in humans. The clinical potential of prostaglandins in the management of conditions associated with increased ocular pressure, e.g. glaucoma, is greatly limited by these side effects.

Certain phenyl and phenoxy mono, tri and tetra nor prostaglandins and their 1-esters are disclosed in European Patent Application 0,364,417 as useful in the treatment of glaucoma or ocular hypertension.

In a series of co-pending United States patent applications assigned to Allergan, Inc. prostaglandin esters with increased ocular hypotensive activity accompanied with no or substantially reduced side-effects are disclosed. The co-pending application Ser. No. 386,835 (filed 27 Jul. 1989), relates to certain 11-acyl-prostaglandins, such as 11-pivaloyl, 11acetyl, 11-isobutyryl, 11-valeryl, and 11-isovaleryl $PGF_{2\alpha}$. Intraocular pressure reducing 15-acyl prostaglandins are disclosed in the co-pending application Ser. No. 357,394 (filed 25 May 1989). Similarly, 11,15- 9,15- and 9,11-diesters of prostaglandins, for example 11,15-dipivaloyl $PGF_{2\alpha}$ are known to have ocular hypotensive activity. See the copending patent applications Ser. No. 385,645 filed 27 Jul. 1990, now U.S. Pat. No. 4,994,274; 584,370 which is a continuation of application Ser. No. 386,312, and 585,284, now U.S. Pat. No. 5,034,413 which is a continuation of application Ser. No. 385,834, where the parent applications were filed on 27 Jul. 1989. The disclosures of these patent applications are hereby expressly incorporated by reference.

SUMMARY OF THE INVENTION

We have found that certain 7-[carboxylalkyl or alkenyl]-6-[alkyl or alkenyl]-3-oxo-2,4-dioxobicyclo[3.2.1] octane and derivatives thereof, e.g. hydroxyl, nitro, amino, amido, azido, oxime, thiol, ether and thiol ether derivatives of said carboxy group are potent ocular hypotensive agents. We have further found the unique ability of several of the compounds described herein to mimic the vasoconstrictor properties of thromboxane A2 and its endoperoxide precursors, without causing concomitant platelet aggregation, provides a diverse variety of medical uses. Their potent vasoconstrictor properties may be safely used in therapy as they do not cause the platelet aggregation and resultant thrombosis that would arise from using known thromboxane mimetics.

The vasoconstrictor properties would substantially reduce blood flow in blood vessels and could be used to prevent hemorrhaging associated with external or internal injuries without the risk of thrombosis. These compounds may also be used as surgical adjuncts to reduce the bleeding from incisions at any anatomical location. Similarly, these compounds would be useful in limiting the bleeding associated with tooth extraction. The ability of these compounds to prevent hemorrhage, without causing platelet aggregation and resultant thrombosis, allows their safe application in systemic diseases where hemorrhage occurs. For example, bleeding from the gastro-intestinal tract associated with hemorrhoids, inflammatory bowel diseases, or gastric and peptic ulcer may be prevented. Bleeding associated with stroke may be prevented. Bleeding associated with stroke may be reduced without causing thrombosis and a potentially fatal complication. Bleeding is also a frequent complication in retinal diseases and surgeries resulting in impaired vision. This would also be amenable to safe treatment by the vascular-selective thromboxane mimetics described herein. Excessive bleeding associated with menstruation, childbirth, and uterine dysfunction may also be safely treated.

The selective vasoconstrictor properties of these compounds may be used to treat systemic hypotension. They may also be employed to restore normal blood pressure in haemorragic, anaphylactic, or septic shock episodes, without the serious risks associated with typical thromboxane mimetics which would result from their pro-aggregatory effects on platelets.

The selective vasoconstrictor properties may also be used to provide local anti-inflammatory effects in tissues such as the eye, skin, and nose. They may also be used to limit plasma exudation in burns and scalds.

A thromboxane-like vasoconstrictor that does not cause platelet aggregation may also be useful in optimizing blood born delivery of drugs and diagnostics in encapsulating vehicles. For example, delivery of drugs or diagnostic substances encapsulated in heat-sensitive or light-sensitive liposomes to the retina may be safely enhanced by agents described herein which selectively produce vasoconstriction.

Finally, the profound ocular hypotensive activity of these cyclic carbonate compounds is unexpected, given that the benchmark thromboxane/endoperoxide mimetic U-46619 (Coleman, R.A., et.al., Br. J. Pharmacol. 73:773-778, 1981) causes ocular hypertension in primates. The compounds herein would, therefore, be useful for treating glaucoma and ocular hypertension. They may also be useful as ocular surgical adjuncts for preventing ocular hypertensive episodes and reducing local bleeding. Moreover, when these compounds are used to treat glaucoma surprisingly, they cause no or significantly lower ocular surface hyperemia than many other compounds having hypotensive activity.

The present invention relates to methods of treating ocular hypertension which comprises administering an effective amount of a 7-[carboxyalkyl or alkenyl]-6-[alkyl or alkenyl]-3-oxo-2,4-dioxobicyclo[3.2.1] octane or a hydroxyl, nitro, amino, amido, azido, oxime, thiol, ether or thiol ether derivative thereof represented by the formula I

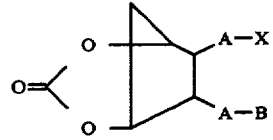

wherein A is an alkylene or alkenylene radical having from two to seven carbon atoms, e.g. about four to six carbon atoms, which radical may be substituted with one or more hydroxy, oxo, alkyloxy or alkylcarboxy groups or said alkylene or alkenylene may have one or more enchained oxo radicals, and B is a methyl radical or a cycloalkyl radical having from three to seven carbon atoms, e.g. about five to six carbon atoms, or an aryl radical, selected from the group consisting of hydrocarbyl aryl and heteroaryl radicals wherein the heteroatom is selected from the group consisting of nitrogen, oxygen and sulfur atoms, and X is selected from the group consisting of halo, nitro, cyano, —COOR$_4$, —CH$_2$OR$_4$, —C(O)N(R$_4$)$_2$, —CH$_2$N(R$_4$)$_2$—CH=N—OH and —CH$_2$SR$_4$ radicals wherein R$_4$ is hydrogen, C$_1$ to C$_{10}$ alkyl, phenyl or benzyl; or a pharmaceutically acceptable salt thereof. For example, A may be a straight chain alkylene radical, e.g. heptylene, or alkenylene radical, e.g. 3-hydroxy-1-heptylenyl, or an ethylenyloxyethylenyl radical and B may be selected from the group consisting of methyl, cyclopentyl, cyclohexyl, phenyl, thienyl, furanyl, pyridyl, etc. B may also be substituted by radicals selected from the group consisting of halo, e.g. fluoro, chloro, etc., nitro, amino, thiol, hydroxy, alkyloxy, alkylcarboxy, etc. Preferably, B is methyl, cyclohexyl or phenyl.

DETAILED DESCRIPTION OF THE INVENTION

The present invention relates to the use of 7-carboxylalkyl or alkenyl]-6-[alkyl or alkenyl]-3-oxo-2,4-dioxobicyclo[3.2.1] octane or a hydroxyl, nitro, amino, amido, azido, oxime, thiol, ether or thiol ether derivative thereof as ocular hypotensives. These therapeutic agents are represented by compounds having the formula I,

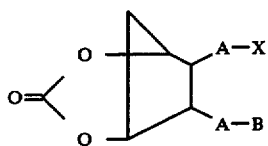

wherein A is an alkylene or alkenylene radical having from two to seven carbon atoms, e.g. about four to six carbon atoms, which radical may be substituted with one or more hydroxy, oxo, alkyloxy or alkylcarboxy groups or said alkylene or alkenylene radical may have one or more enchained oxo radicals, and B is a methyl radical or a cycloalkyl radical having from three to seven carbon atoms, e.g. about five to six carbon atoms, or an aryl radical, selected from the group consisting of hydrocarbyl aryl and heteroaryl radicals wherein the heteroatom is selected from the group consisting of nitrogen, oxygen and sulfur atoms, and X is selected from the group consisting of halo, nitro, cyano, —COOR$_4$, —CH$_2$OR$_4$, —C(O)N(R$_4$)$_2$, —CH$_2$N(R$_4$)$_2$ —CH=N—OH and —CH$_2$SR$_4$ radicals wherein R$_4$ is hydrogen, C$_1$ to C$_{10}$ alkyl, phenyl or benzyl. For example, A may be a straight chain alkylene radical, e.g. heptylene, or alkenylene radical, e.g. 3-hydroxy-1-heptylenyl, or an ethylenyloxyethylenyl radical and B may be selected from the group consisting of methyl, cyclopentyl, cyclohexyl, phenyl, thienyl, furanyl, pyridyl, etc. B may also be substituted by radicals selected from the group consisting of halo, e.g. fluoro, chloro, etc., nitro, amino, thiol, hydroxy, alkyloxy, alkylcarboxy, etc. Preferably, B is methyl, cyclohexyl or phenyl; or a pharmaceutically-acceptable salt thereof.

For the purpose of this invention, unless further limited, the term "aliphatic" means linear and branched alkylene and alkenylene radicals, the terms "alkylene" and "alkenylene" mean divalent radicals derived from alkanes and alkenes, respectively. The term "alkyl" refers to alkyl groups having from one to ten carbon atoms, the term "cycloalkyl" refers to cycloalkyl groups having from three to seven carbon atoms, the term "aryl" refers to aryl groups having from four to ten carbon atoms. The term "saturated or unsaturated acyclic hydrocarbon group" is used to refer to straight or branched chain, saturated or unsaturated hydrocarbon groups having from one to about six, preferably one to about four carbon atoms. Such groups include alkyl, alkenyl and alkynyl groups of appropriate lengths, and preferably are alkyl, e.g. methyl, ethyl, propyl, butyl, pentyl, or hexyl, or an isomeric form thereof.

More preferably the method of the present invention comprises administering a 7-[carboxyalkyl or alkenyl]-6[alkyl or alkenyl]-3-oxo-2,4-dioxobicyclo[3.2.1] octane or a hydroxyl, nitro, amino, amido, azido, oxime, thiol, ether and thiol ether derivative thereof represented by the formula II

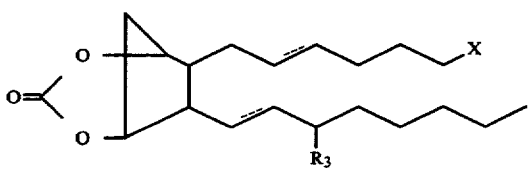

wherein either the α or ω chain may be unsaturated, i.e. the dashed bonds represent a single bond or a double bond which can be in the cis or trans configuration and R$_3$ is =O, —OH or —O(CO)R$_6$; wherein R$_6$ is a saturated or unsaturated acyclic hydrocarbon group having from 1 to about 20 carbon atoms, or —(CH$_2$)$_m$R$_7$ wherein m is 0–10, preferably 0–4; and R$_7$ is an aliphatic ring from about 3 to about 7 carbon atoms, or an aryl or heteroaryl ring, as defined above; or a pharmaceutically acceptable salt thereof. Preferably the derivative used in the above method of treatment is a compound of formula III.

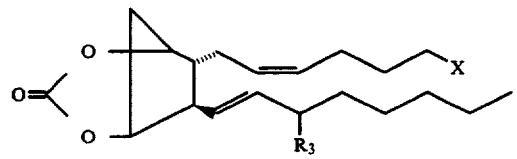

wherein hatched lines indicate ct configuration, solid triangles are used to indicate β configuration.

As an aromatic ring, R$_7$ preferably is phenyl, and the heteroaromatic rings have oxygen, nitrogen or sulfur as a heteroatom, i.e., R$_7$ may be thienyl, furanyl, pyridyl, etc.

In a further aspect, the present invention relates to pharmaceutical compositions comprising a therapeutically effective amount of a compound of formulae (I), (II), or (III) wherein the symbols have the above meanings, or a pharmaceutically acceptable salt thereof in admixture with a non-toxic, pharmaceutically acceptable liquid vehicle.

In a still further aspect, the present invention relates to 7-[carboxylalkyl or alkenyl]-6-[alkyl or alkenyl]-3-oxo-2,4-dioxobicyclo[3.2.1] octane, or hydroxyl, nitro, amino, amido, azido, oxime, thiol, ether or thiol ether derivatives thereof, of the above formulae, wherein the substituents and symbols are as defined hereinabove, or a pharmaceutically acceptable salt of such compounds.

Preferred representatives of the compounds within the scope of the present invention are the compounds of formula III wherein X is —COOR$_4$, —CH$_2$OH and —C(O)N(R$_4$)$_2$, wherein R$_4$ is defined above, and the pharmaceutically acceptable salts thereof. Specific compounds within the scope of this invention are as follows:

7-[6-carboxy-2-cis-hexenyl]-6-[3α-hydroxy- 1-transoctenyl]-3-oxo-2,4-dioxobicyclo[3.2.1]octane 7-[6-carbomethoxy-2-cis-hexenyl-6-[3α-hydroxy-1-trans-octenyl]-3-oxo-2,4-dioxobicyclo[3.2.1] octane 7-[6-carbomethoxy-2-cis-hexenyl-6-[3α-pivaloyloxy-1- trans-octenyl]-3-oxo-2,4-dioxobicyclo[3.2.1] octane 7-[7-hydroxy-2-cis-heptenyl-6-[3α-hydroxy-1-transoctenyl]-3-oxo-2,4-dioxobicyclo[3.2.1] octane 7-[6-carbobenzoxy-2-cis-hexenyl-6-[3α-hydroxy-1-trans-octenyl]-3-oxo-2,4-dioxobicyclo[3.2.1] octane 7-[6-carbobenzoxy-2-cis-hexenyl]-6-[3α-pivaloyloxy-1-trans-octenyl]-3-oxo-2,4-dioxobicyclo[3.2.1 ]octane 7-[6-carboamino-2-cis-hexenyl-6-[3α-hydroxy-1-trans-octenyl]-3-oxo-2,4-dioxobicyclo[3.2.1 ]octane 7-[6-carboisopropylamino-2-cis-hexenyl]-6-[3α-hydroxy-1 -trans-octenyl]-3-oxo-2,4-dioxobicyclo [3.2.1]octane 7-[6-carboxy-2-cis-hexenyl]-6-[3α-pivaloloxy- 1 -transoctenyl]-3-oxo-2,4-dioxobicyclo [3.2.1] octane A pharmaceutically acceptable salt is any salt which retains the activity of the parent compound and does not impart any deleterious or undesirable effect on the subject to whom it is administered and in the context in which it is administered. Such salts are those formed with pharmaceutically acceptable cations, e.g., alkali metals, alkali earth metals, etc.

Pharmaceutical compositions may be prepared by combining a therapeutically effective amount of at least one compound according to the present invention, or a pharmaceutically acceptable salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, (sodium EDTA) although other chelating agents may also be used in place of or in conjunction with it.

The ingredients are usually used in the following amounts:

| Ingredient | Amount (% w/v) |
|---|---|
| active ingredient | about 0.001–5 |
| preservative | 0–0.10 |
| vehicle | 0–40 |
| tonicity adjustor | 0–10 |
| buffer | 0.01–10 |
| pH adjustor | q.s. pH 4.5–7.5 |
| antioxidant | as needed |

| Ingredient | Amount (% w/v) |
|---|---|
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for dropwise application are usually made of suitable inert, nontoxic plastic material, and generally contain between about 0.5 and about 15 ml solution. One package may contain one or more unit doses.

Especially preservative-free solutions are often formulated in non-resealable containers containing up to about ten, preferably up to about five units doses, where a typical unit dose is from one to about 8 drops, preferably one to about 3 drops. The volume of one drop usually is about 20–35 µl.

This invention is further illustrated by the following non-limiting examples.

EXAMPLE 1

CYCLOPENTANE HEPTENOIC ACID, 5-CIS-2-(3A-t-B UTYLDIMETHYL-SILYLOXY-1-TRANS-OCTENYL)-3,5-DIHYDROXY, [1α, 2β, 3α, 5α] METHYL ESTER.

PGF2α (542 mg, 1.53 mmol) was dissolved in ethylether (Et$_2$O) (20 mL) and cooled to 0° C. A solution of CH$_2$N$_2$ in Et$_2$O was added dropwise to the above suspension until a yellow color persisted. The solution was warmed to 25° C. for 0.5 h and then concentrated in vacuo to yield PGF 2α methyl ester as an oil.

The crude ester was heated at reflux with n-butyl boronic acid (0.188 g, 1.84 mmol) in CH$_2$Cl$_2$(3.1 mL) for 2h. The volatiles were removed under vacuum to yield the crude boronate ester which was immediately diluted with CH$_2$Cl$_2$ (3 mL) and cooled to 0° C. 2,6-Lutidine (0.43 mL, 3.7 mmol) was added followed by t-butyldimethylsilyl trifluoromethanesulfonate (0.67 mL, 2.9 mmol). The reaction solution was then warmed to 23° C. for 16h, concentrated, and rediluted with methanol (40mL). After stirring for 24 h, the methanol was removed under vacuum and the residue was purified by FCC (2:1 hexane (hex)/ethyl acetate (EtOAc), silica gel) to yield (0.697, 92% yield) of the named product as an oil.

EXAMPLE 2

7-[6-CARBOMETHOXY-2-CIS-HEXENYL]-6-[3α-t-BUTYLDIMETHYLSILYLOXY-1-TRANS-OCTENYL]-3-OXO-2,4-DIOXOBICYCLO [3.2.1] OCTANE 149 mg (0.318 mmol) of the compound of Example 1 were dissolved in 1.6 ml of CH$_2$Cl$_2$ and cooled to at −78° C. 0.154 mL (0.6 mmol) of pyridine were then added and stirring was continued for 5 minutes. 48 mg (0.5 mmol) of triphosgene dissolved in 1 mL CH$_2$Cl$_2$ was slowly added and the resulting mixture was stirred for an additional hour before being allowed to slowly warm to room temperature. After standing overnight the reaction was quenched with saturated aqueous NH₄Cl, diluted with EtOAc and the resulting reaction mixture was worked up washing the organic portion with 1 N HCl NaHCO₃ and brine. The organic layer was dried over anhydrous MgSO₄ to yield 149 mg of a crude fraction including the named compound.

EXAMPLE 3

7-[7-HYDROXY-2-CIS-HEPTENYL]-6-[3α-t-BUTYLDIMETHYLSILYLOXY-1-TRANS-OCTENYL]-3-OXO-2,4-DIOXOBICYCLO [3.2.1] OCTANE 73 mg (0.143 mmol) of the compound of Example 2 were dissolved in a 0.28 mL of ethylether (Et₂O) and then 3.0 mg of lithium borohydride (LiB H4) were added and the mixture stirred at 23° C. overnight. The reaction was quenched using 2.0 N NaOH and the resulting reaction mixture was worked up by consecutive treatment with EtOAc and brine. The resulting organic layer was concentrated in vacuo and dried over anhydrous MgSO₄ to yield 63 mg of the named compound.

EXAMPLE 4

7-[7-HYDROXY-2-CIS-HEPTENYL]-6-[3α-HYDROXY-1-TRANS-OCTENYL]-3-OXO-2,4-DIOXOBICYCLO [3.2.1] OCTANE 14 mg (0.03 mmol) of the compound of Example 3 were dissolved in THF and 0.045 mL of a 1.0 M solution of tetrabutyl ammonium fluoride (Bu₄NF) were added. After stirring under argon at room temperature for 5 hours the resulting reaction mixture was worked up by dilution with EtOAc and washing with H₂O. The organic layer was dried over anhydrous MgSO₄, filtered, and concentrated in vacuo to yield 83 mg of crude product. The crude product was purified by consecutive elution on silica gel with a solution of 60% EtOAc in hexane to yield the named compound.

EXAMPLE 4a

CYCLOPENTANE HEPTENOIC ACID, 5-CIS-2-(3-t-BUTYLDIMETHYLSILYLOXY-1-TRANS-OCTENYL)-3,5-DIHYDROXY, [1α, 2β, 3β, 5α] BENZYL ESTER

A solution of the ester of Example 1 (556 mg, 1.17 mmol) in 0.5 N aqueous lithium hydroxide (3.5 mL, 1.76 mmol) and THF (7.0 mL) was stirred at 23° C. for 24 h and acidified with 10% citric acid. The mixture was extracted with EtOAc and the combined organics were dried (MgSO₄), filtered and concentrated in vacuo.

The crude residue was treated with O-benzyl-N,N'-diisopropylisourea (0.41g, 1.76 mmol) and heated to 65° C. in benzene (7.0 mL) for 24 h. The reaction was cooled to room temperature and stripped of the solvent. FCC (2:1 hex/EtOAc) of the residue gave 553 mg (85%) of the named compound.

EXAMPLE 5

7-[6-CARBOBENZOXY-2-CIS-HEXENYL]-6-[3α-t-UTYLDIMETHYLSILYLOXY-1-TRANS-OCTENYL]-3-OXO-2,4-DIOXOBICYCLO [3.2.1] OCTANE 330 mg (0.591 mmol) of the compound of Example 4a were treated in accordance with the procedure of Example 2 to yield 235.7 mg (68% yield) of the named compound.

EXAMPLE 6

7-[6-CARBOBENZOXY-2-CIS-HEXENYL]-6-[3α-HYDROXY-1-TRANS-OCTENYL]-3-OXO-2,4-DIOXOBICYCLO [3.2.1] OCTANE 60 mg (0.1027 mmol) of the compound of Example 5 in 1.0 mL of THF was treated with 0.2054 mL a 1.0 M solution of Bu₄NF and stirred at 23° C. for 16 hours. The reaction mixture was diluted with EtOAc and washed, consecutively, with H₂O and brine and dried over anhydrous MgSO₄. The dried organic phase was filtered and the filtrate concentrated under vacuum. Elution on silica gel with a 1:1 mixture of hexane and EtOAc yielded 29.7 mg (62% yield) of the named compound.

EXAMPLE 7

7-[6-CARBOXY-2-CIS-HEXENYL]-6-[3α-HYDROXY-1-TRANS-OCTENYL]-3-OXO-2,4-DIOXOBICYCLO [3.2.1] OCTANE 25 mg (0.0531 mmol) of the compound of Example 6 was mixed with 8 mg of a catalyst comprising 10% Palladium, by weight, on carbon and 0.25 mL of 1-methyl-1,4cyclohexadiene in 1.0 mL of methanol and heated at 35° C. In 20 minutes the reaction was complete and the reaction mixture was diluted with $CH_2Cl_2$ and filtered. The filtrate was concentrated in vacuo and eluted on silica gel with EtOAc to yield 20 mg (99% yield) of the named compound.

EXAMPLE 8

CYCLOPENTANE HEPTENOIC ACID, 5-CIS-2-(3α-HYDROXY-1-TRANS-OCTENYL)-3,5-HYDROXY, [1α, 2β, 3α, 5α] BENZYL ESTER 1.75 g (4.93 mmol) of the prostaglandin $F_{2α}$ et were mixed with 1.73 g (7.40 mmol) of 0-benzyl-N,N'-diisopropylisourea in 25 mL of benzene and heated to 65° C. to yield a crude fraction containing the named compound. After separation of the crude from the solvent, treatment by consecutive elution on silica gel with a 1:1 mixture of hexane and EtOAc followed by 95:5 mixture of EtOAc and methanol gave 2.08 g (95% yield) of the named compound.

EXAMPLE 9

CYCLOPENTANE HEPTENOIC ACID, 5-CIS-2-(3α-PIVALOYLOXY-1-TRANS-OCTENYL)-3,5-DIHYDROXY, [1α, 2β3α, 5α] BENZYL ESTER 1.13 gm (2.54 mmol) of the compound of Example 8 and 0.39 g (3.81 mmol) of n-butylboronic acid in 28 mL of toluene were heated at reflux for 72 hours with azeotropical removal of water. The reaction mixture was cooled to 23° C. and concentrated in vacuo. The residue was diluted with $CH_2Cl_2$ and reacted with 0.77 mL (3.81 mmol) of trimethylacetylchloride, 1.06 mL (7.63mmol) of triethylamine and 155 mg (1.27 mmol) of DMAP (4dimethylaminopyridine) and stirred at 23° C. for 48 hours. The resulting reaction mixture was concentrated, dissolved in methanol and stirred overnight. The methanol was removed in vacuo and the residue was purified by elution on silica gel with a 2:1 mixture of hexane and EtOAc to afford 0.87 gm (65% yield) of the named compound was obtained.

EXAMPLE 10

CYCLOPENTANE HEPTENOIC ACID, 5-CIS-2-(3α-PIVALOYLOXY-1-TRANS-OCTENYL)-3-HYDROXY, 5-IMIDAZOLYLOXY [1α, 2β,3α,5α ] BENZYL ESTER 211 mg (0.399 mmol) of the compound of Example 9 and 77.7 mg (0.479 mmol) of 1,1-carbonyldiimidazole were dissolved in 1.0 mL of $CH_2Cl_2$ and stirred for 24 hours at 23° C. to yield the named compound.

EXAMPLE 11

7-[6-CARBOBENZOXY-2-CIS-HEXENYL]-6-[3α-PIVALOYLOXY-1-TRANS-OCTENYL]-3-OXO-2,4-DIOXOBICYCLO[3.2.1 ]OCTANE 0.133 mmol of the compound of Example 10 and 0.14 mL (1.33 mmol) of t-butylamine dissolved in $CH_2Cl_2$ were heated to 45° C. for 48 hours. The reaction mixture was cooled to room temperature, concentrated in vacuo and ehted on silica gel with a 3:1 mixture of hexane and EtOAc to yield 31 mg (42% yield) of the named compound.

EXAMPLE 12

7-[6-CARBOXY- 2-CIS-HEXENYL ]-6-[3α-PIVALOYLOXY-1-TRANS-OCTENYL]-3-OXO 2,4-DIOXOBICYCLO[3.2.1] OCTANE

The compound of Example 11 was treated according to the procedure of Example 7 to yield the named compound.

EXAMPLE 13

CYCLOPENTANE HEPTENAMIDE, 5-CIS-2-[3α-t-BUTYLDIMETHYLSILYLOXY-1-TRANS-OCTENYL)-3,5 DIHYDROXY, [1α, 2β, 3α, 5α]

460 mg (0.954 mmol) of the compound of Example 1 was reacted with an excess of NH3 in 6.0 mL of methanol to yield a solution including the named compound. The excess solvent and unreacted NH3 were evaporated and the residue was purified by elution on silica gel, consecutively, with 100% EtOAc followed by a 9:1 mixture of $CH_2Cl_2$ and methanol to yield 395 mg (89% yield) of the named compound.

EXAMPLE 14

7-[6-CARBOAMINO-2-CIS-HEXENYL]-6-[3α-t-BUTYLDIMETHYLSILYLOXY-1-TRANS-OCTENYL]-3-OXO-2,4-DIOXOBICYCLO[3.2.1]OCTANE 256 mg (0.548 mmol) of the compound of Example 13, 5 mg (0.040 mmol) of 4-dimethylamino pyridine (DMAP) and 98 mg. (0.602 mmol) of 1,1 carbonyldiimidazole were reacted in 1.5 ml of $CH_2Cl_2$, for 24 hours at 23° C. The resulting reaction solution was concentrated in vacuo and the residue purified by elution with 100% EtOAc. The resulting reaction product was stirred with 71 uL DBU (0.474 mmol) in 1.0 mL of benzene for 24 hours at 23° C. After concentration in vacuo and elution on silica gel with a 2:1 mixture of EtOAc and hexane, 25 mg (10% yield) of the named compound were obtained.

EXAMPLE 15

7-[6-CARBOAMINO-2-CIS-HEXENYL]-6-[3α-HYDROXY-1-TRANS-OCTENYL]-3-OXO-2,4-DIOXOBICYCLO[3.2.1] OCTANE

The compound of Example 14 was converted into the named compound at 95% yield by the procedure of Example

EXAMPLE 16

7-[6-CARBOXY-2-CIS-HEXENYL ]-6-[3α-t-BUTYLDIMETHYLSILYLOXY-1-TRANS-OCTENYL]-3-OXO -2,4-DIOXOBICYCLO[3.2.1 ]OCTANE 156 mg (0.267 mmol) of the compound of Example 5 were treated in accordance with the procedure as Example 7 to yield the corresponding carboxylic acid (99%) yield).

EXAMPLE 17

7-[6-CARBOISOPROPYLAMINO-2-CIS-HEXENYL]-6-[3α-HYDROXY- 1-TRANS-OCTENYL]-3-OXO-2,4-DIOXOBICYCLO [3.2.1] OCTANE 75 mg (0.151 mmol) of the compound of Example 16 in $CH_2Cl_2$ were reacted with 1.5 mL of $SOCl_2$ at 0° C. for 1 h. 69 mg (1.17 mmol) of isopropylamine were added and the resultant solution was warmed to 23° C. for 16 h to yield a reaction mixture which upon removal of the excess solvent and purification by elution on silica gel with a 1:1 mixture of hexane and EtOAc gave 4.8 mg (8% yield) of the named compound.

EXAMPLE 18A

CYCLOPENTANE HEPTENOIC ACID, 5-CIS-2-(3α-PIVALOYLOXY-1-TRANS-OCTENYL)-3,5-DIHYDROXY, [1α, 2β, 3α, 5α] METHYL ESTER $PGF_{2α}$ methyl ester (prepared as described in Example 1) was treated according to the procedure of Example 9 to yield the named compound.

EXAMPLE 18B

CYCLOPENTANE HEPTENOIC ACID, 5-CIS-2-(3α-PIVALOYLOXY-1-TRANS-OCTENYL)-3-HYDROXY, 5-IMIDAZOLYOXY, [1α, 2β, 3α, 5α] METHYL ESTER

A solution of the compound of Example 18A (75 mg 0.166 mmol) in THF (1.0 mL) was heated to 50° C. and triphosgene (16.4 mg, 0.0553 mmol) was added. After 2 h imidazole (22.6 mg, 0.332 retool) was added and a white precipitate formed immediately. The reaction was stirred an additional 16 h, allowed to cool to room temperature, and concentrated in vacuo. Purification of the residue by FCC (1:1 hex/EtoAc, silica gel) afforded the 45.3 mg of the named compound, i.e 50% yield.

EXAMPLE 18C

7-[6-CARBOMETHOXY-2-CIS-HEXENYL]-6-[3α-PIVALOYLOXY-1-TRANS-OCTENYL]-3-OXO-2,4-DIOXOBICYCLO [3.2.1]OCTANE

A solution of the compound of Example 18B (17.4 mg, 0.032 mmol) in benzene (0.75 mL) was treated with 1,8diazabicyclo [5.4.0] undec-7-ene (DBU) (24 μL, 0.159 mmol) at 23° C. After 12 h the reaction solution was concentrated in vacuo and the residue was purified by FCC (1:1 hex/EtoAc, silica gel) to give 12.9 mg (85% yield) of the named compound.

PROSTANOID RECEPTOR ACTIVITY

Activity at different prostanoid receptors was measured in vitro in isolated smooth muscle preparations. FP-activity was measured as contraction of the isolated feline iris sphincter. $EP_1$-activity was measured as contraction of the longitudinal smooth muscle of the isolated guinea pig ileum. $EP_3$-activity was measured as inhibition of the twitch response induced by electrical field stimulation in the isolated guinea pig vas deferens and as contraction of the longitudinal smooth muscle of the isolated chick ileum. TP-vasoconstrictor activity was measured as contraction of rings of the isolated rat thoracic aorta. Effects on platelets from healthy human donors were measured by incubating platelet-rich plasma with the compounds described herein. Inhibition of aggregation was determined by the ability of the compounds described herein to inhibit platelet aggregation in platelet-rich plasma induced by 20 μM ADP. The activity profile of various compounds is reported in Table 1.

In addition, inhibition by the thromboxane A2-receptor antagonist SQ29,548 ([b 1S-[1α, 2α (5Z), 3α, 4α]]-7-[3-[[2-[phenylamino)carbonyl]hydrazino]methyl]-7-oxabicyclo[2.2.1]hept-2-yl]-5-heptenoic acid) of vasoconstrictor activity was investigated. For that purpose, activity of the compound of Example 4, the compound of Example 7, and U-46619 (9,11-dideoxy-9α, 11α-methanoepoxy prostaglandin $F_{2α}$), a potent and stable thromboxane $A_2$ analog, was measured in rings of the isolated rat thoracic aorta, first in the absence and then in the presence of SQ29,548 (1 μM). The results are has, therefore, been concluded that there is no convincing evidence that subtypes of the TP-receptor exist (Jones, R.L., Wilson, N.tt., Armstrong, R.A., Tymkewycz, P.M. Colloque INSERM ..152:335 344, 1987). Examples 4, 15 and 16 exhibit pronounced activity in contracting vascular smooth muscle but have no or minimal ability to cause platelet aggregation.

Further evidence is provided below to demonstrate that the ability of examples 4, 15 and 16 to cause contraction of vascular smooth without causing platelet aggregation involves selective stimulation of a subtype of TP-receptor present on vascular smooth muscle. 1. A TP-receptor antagonist blocks the effect of agonists which are selective for the vascular TP-receptor (Example 4) and non-selective with respect to vascular and platelet TP-receptors (Example 7, U-46619), see Table 2. This shows that Example 4 and its congeners, which show selectivity for contracting vascular smooth muscle, produce their effect by interacting with a subtype of TP-receptor as opposed to some other type of eicosanoid receptor.

2. The compound Example 4 neither causes platelet aggregation nor inhibits the ability of U-46619 or Example 7 to cause platelet aggregation, see Table 3. Moreover, Example 4 did not inhibit ADP or arachidonic acid induced platelet aggregation (Table 4) and, therefore, its activity cannot be ascribed to a mechanism which opposes the aggregatory e.g., behaving as a prostacyclin or prostaglandin D2 mimetic, inhibition of cyclooxygenase.

Thus, it appears that certain examples of formula III selectively constrict smooth muscle by stimulating a TP-receptor subtype which exists on smooth muscle but not on platelets.

TABLE 1

| | EFFECT OF EXAMPLES OF FORMULA III AT DIFFERENT PROSTANOID RECEPTOR SUBTYPES | | | | | | |
|---|---|---|---|---|---|---|---|
| | COMPOUND $EC_{50}$ (nM) VALUES AT PROSTANOID RECEPTOR SUBTYPES | | | | | | |
| | FP (Cat Iris) | $EP_1$ (Guinea Pig Ileum) | $EP_{3(c)}$ (Guinea Pig vas deferens) | $EP_{3(d)}$ (Chick Ileum) | $TP_{vasc}$ (Rat Aorta) | Platelets (Human) Aggregation | Inhibition of Aggregation |
| Example 7 | 433 | 1,240 | 282 | 245 | 0.23 | 24 | N/A |
| Example 4 | 485 | N/A | 2,930 | >$10^4$ | 1.0 | >$10^4$ | N/A |
| Example 16 | 3,020 | | | | 324 | N/A | N/A |
| Example 15 | 387 | | | | 58 | 3,110 | N/A |

$EC_{50}$ (nM) = nM concentration required to produce a 50% of maximal response reported in Table 2.

EXAMPLE 19

PHARMACOLOGICAL SELECTIVITY FOR A TP-RECEPTOR SUBTYPE PRESENT ON VASCULAR SMOOTH MUSCLE

Examination of Table 1 reveals an unexpected and unique trend in biological activity associated with certain examples of formula III. Typically, thromboxane (TP-) receptor agonists indiscriminately cause both platelet aggregation and smooth muscle contraction. It

TABLE 2

EFFECT OF THE THROMBOXANE (TP)-RECEPTOR ANTAGONIST SQ 29548 ON CONTRACTION OF THE RAT AORTA PRODUCED BY EXAMPLES OF FORMULA III

| | $EC_{50}$ at $TP_{vasc}$-RECEPTOR | |
|---|---|---|
| COMPOUND | −SQ29,548 | +SQ29,548 |
| Example 7 | 2 | 325 |
| Example 4 | 0.9 | 454 |
| U-46619 | 13 | 8,080 |

TABLE 4

Effect of Example 4 Antagonist-Induced Platelet Aggregation Induced by Arachidonic

| Acid and ADP Agonist: | Agonist Response: % of max response | $10^{-7}$ M Example 4 pretreatment | $10^{-6}$ M Example 4 pretreatment |
|---|---|---|---|
| 800 μM Arachidonic Acid | 101.6 + 1.3 | 98.0 + 1.8 | 98.8 + 1.1 |
| 20 μM ADP | 100 + 0 (standard) | 99.9 + 1.4 | 97.6 + 1.8 |
| 2 μM ADP | 73.8 + 11.17 | 68.3 + 12.9 | 73.1 + 14.3 |

TABLE 3

Effect of Example 4 on Example 7 and U46619-induced Platelet Aggregation

| Agonist: | Agonist Response: % of max response | 10-7 M Example 4 pretreatment | 10-6 M Example 4 pretreatment |
|---|---|---|---|
| 10-9 Example 7 | 0 | | |
| 10-8 Example 7 | −7.9 + 1.3 | −8.4 + 0.9 | −8.0 + 2.9 |
| 3.3 × 10$^{-8}$ | −8.8 + 1.3 | −9.0 + 1.6 | −7.3 + 0.7 |
| 10-7 Example 7 | 100.5 + 2.2 | 97.8 + 1.7 | 99.5 + 1.7 |
| 10-6 Example 7 | 103.0 + 1.9 | 95.3 + 0.9 | 96.5 + 0.9 |
| 10-8 U46619 | 0 | | |
| 10-7 U46619 | −7.0 + 1.1 | −5.5 + 1.1 | −5.6 + 0.9 |
| 3.3 × 10$^{-7}$ U46619 | 97.7 + 1.6 | 93.8 +2.3 | 94.2 +2.8 |
| 10-6 U46619 | 100.0 + 1.9 | 94.6 +2.6 | 96.0 + 0.8 |

EXAMPLE 20

EFFECTS ON INTRAOCULAR PRESSURE

The effects of four examples of Formula III and the thromboxane mimetic U-46619 on intraocular pressure are provided in the following tables. The compounds were prepared at the said concentrations in a vehicle comprising 0.1% polysorbate 80 and 10 mM TRIS base. Dogs and monkeys were treated by administering 25 ul to the ocular surface, the contralateral eye received vehicle as a control. Intraocular pressure was measured by applanation pneumatonometry. Experiments were performed with dogs and monkeys. Dog intraocular pressure was measured immediately before drug administration and at 2, 4 and 6 hour thereafter. Additional studies in monkeys were performed over a 5 day period and drug was administered at times 0, 6, 24, 30, 48, 54, 72, 78, and 96 hours. Monkey intraocular pressure was recorded just before drug administration on each day and at the 2 and 4 hour time intervals between dosing.

The examples of Formula III examined showed a pronounced ocular hypotensive effect in both dogs and monkeys (Tables 5 and 6). In contrast, the thromboxane/endoperoxide mimetic U-46619 produced an increase in intraocular pressure. ,Thus, the cyclic carbonate derivatives described herein caused a profound decrease in intraocular pressure which was unexpected given the absence of ocular hypotensive activity associated with U-46619. Since the in vitro pharmacological effects of the cyclic carbonate analogs (a) cannot be attributed to stimulation of other known prostanoid receptors and (b) are susceptible to a thromboxane antagonist, it is concluded that the ocular hypotensive activity of these compounds is related to selective stimulation of a thromboxane receptor subtype.

TABLE 5

The effect of compounds of Formula III and U-46619 (9,11-dideoxy-9α,11α, methanoepoxy prostaglandin F$_{2\alpha}$) on dog intraocular pressure.

| FORMULA III | (Dose %) | INTRAOCULAR PRESSURE CHANGES AT PREDETERMINED TIMES (hr) AFTER DOSING | | |
|---|---|---|---|---|
| | | 2 HR | 4 HR | 6 HR |
| U-46619 | 0.1% | +0.86 | +1.75 | +2.7 |
| Example 7 | 0.01% | −9.7** | −11.4** | −11.25** |
| Example 4 | 0.1% | −6.7** | −7.7** | −8.5** |
| Example 11 | 0.1% | −6.9** | −7.7** | −9.4** |
| Example 12 | 0.1% | −3.8** | −4.7** | −6.9** |

**p < 0.01, Student's paired t test

TABLE 6

The effect of compounds of Formula III and U-46619 (9,11-dideoxy - 9α, 11α, methanoepoxy prostaglandin F$_{2\alpha}$) on monkey intraocular pressure.

| Formula III | Dose (%) | INTRAOCULAR PRESSURE CHANGES AT PREDETERMINED TIMES (HR) AFTER DOSING | | | | | | | | | |
|---|---|---|---|---|---|---|---|---|---|---|---|
| | | 0 | 2 | 4 | 6 | 24 | 26 | 28 | 30 | 48 | 50 | 52 |
| U-46619 | | 0 | 2.0** | 0.3 | 1.0* | | | | | | | |
| Example 7 | 0.01% | 0 | −0.4 | 0 | 0 | −1.0 | 3.2* | −4.6** | −3.2 | −1.8 | −3.8 | −4.0* |

| Formula III | Dose (%) | INTRAOCULAR PRESSURE CHANGES AT PREDETERMINED TIMES (HR) AFTER DOSING | | | | | | | |
|---|---|---|---|---|---|---|---|---|---|
| | | 54 | 72 | 74 | 76 | 78 | 96 | 98 | 100 |
| U-46619 Example 7 | 0.01% | −4.2* | 4.2* | −2.0 | −3.2 | −4.0 | −2.0 | −2.2 | −3.2* |

*p < 0.05 Students' paired t test
**p < 0.01

The foregoing description details specific methods and compositions that can be employed to practice the present invention, and represents the best mode contemplated. However, it is apparent from one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same results. Thus, however detailed the foregoing may appear in text, it should not be construed as limiting the overall scope hereof; rather, the ambit of the present invention is to be governed only by the lawful construction of the appended claims.

We claim:

1. The method of treating ocular hypertension which comprises applying a sufficient amount of the compound of formula III

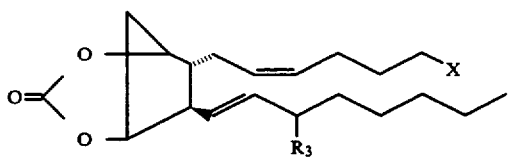

(III)

wherein hatched lines indicate ct configuration, Rhd 3 is =O, —OH or —O(CO)—R₆ wherein R₆ is a saturated or unsaturated acyclic hydrocarbon group having from 1 to about 20 carbon atoms, X is selected from the group consisting of —COOR₄, —CH₂OR₄, —CH₂N(R₄)₂ and -C(O)N(R₄)₂ wherein R₄ is hydrogen, C₁ to C₁₀ alkyl, phenyl or benzyl; or a pharmaceutically acceptable salt thereof, solid triangles are used to indicate β configuration.

2. The method of claim 1 wherein the compound is selected from the group consisting of 7-[6-carboxy-2-cis-hexenyl]-6-[3α-hydroxy- 1-trans-octenyl]-3-oxo-2,4-dioxobicyclo[3.2.1]octane 7-[6-carbomethoxy-2-cis-hexenyl]-6-[3α-hydroxy-1-trans-octenyl]-3-oxo-2,4-dioxobicyclo[3.2.1]octane 7-[6-carbomethoxy-2-cis-hexenyl ]-6-[3α-pivaloxy-1-trans-octenyl]-3-oxo-2,4-dioxobicylo[3.2.1]octane 7-[7-hydroxy-2-cis-heptenyl]-6-[3α-hydroxy- 1-trans-octenyl]-3-oxo-2,4-dioxobicyclo[3.2.1]octane 7-[6-carbobenzoxy-2-cis-hexenyl]-6-[3ct-hydroxy-1-trans-octenyl]-3-oxo-2,4-dioxobicyclo 7-[6-carboamino-2-cis-hexenyl]-6-[3α-hydroxy- 1-trans-octenyl]-3-oxo-2, 4-dioxobicyclo [3.2.1]octane 7-[6-carboisopropylamino-2-cis-hexenyl]-6-[3α-hydroxy- 1-trans-octenyl]-3-oxo -2,4-dioxbicyclo[3.2.1] octane 7-[6-carboxy-2-cis-hexenyl]-6-[3α-pivaloyloxy- 1-trans-octenyl]-3-oxo -2,4-dioxobicyclo[3.2.1]octane 7-[6-carboxbenzoxy-2-cis-hexenyl]-6-[3α-pivaloyloxy-1-trans-octenyl]-3-oxo-2,4-dioxobicyclo[3.2.1]octane.

3. A pharmaceutical composition for treating ocular hypertension which comprises a therapeutically-effective amount of a compound of formula III

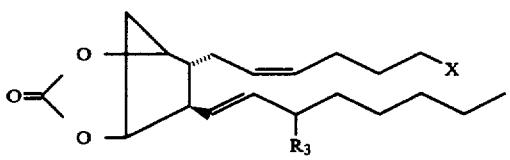

(III)

wherein hatched lines indicate α configuration R₃ is =O, —OH or —O(CO)—R₆ wherein R₆ is a saturated or unsaturated acyclic hydrocarbon group having from 1 to about 20 carbon atoms, X is selected from the group consisting of —COOR₄, —CH₂OR₄, —CH₂N(R₄)₂ and —C(O)N(R₄)₂ wherein R₄ is hydrogen, C₁ to C₁₀ alkyl, phenyl or benzyl; or a pharmaceutically acceptable salt thereof, solid triangles are used to indicate β configuration.

4. A pharmaceutical composition of claim 3 wherein the compound is selected from the group consisting of 7-[6-carboxy-2-cis-hexenyl]-6-[3α-hydroxy- 1-trans-octenyl]-3-oxo-2,4-dioxobicyclo[3.2.1 ]octane 7-[6-carboxy-2-cis-hexenyl]-6-[3α-pivaloxy- 1-trans-octenyl]-3oxo-2,4-dioxobicyclo[3.2.1]octane 7-[6-carbomethoxy-2-cis-hexenyl ]-6-[3α-hydroxy-1-trans-octenyl]-3-oxo-2,4-dioxobicyclo[3.2.1 ]octane 7-[7-hydroxy-2-cis-heptenyl]-6-[3α-hydroxy- 1-trans-octenyl]-3-oxo-2,4-dioxobicyclo[3.2.1]octane 7-[6-carbobenzoxy-2-cis-hexenyl ]-6-[3α-hydroxy-1-trans-octenyl]-3-oxo-2,4-dioxobicyclo[3.2.1]octane s-octenyl]-3-oxo-2,4-dioxobicyclo [3.2.1] octane 7-[6-carboamino-2-cis-hexenyl]-6-[3α-hydroxy-1-trans-octenyl]-3-oxo-2,4-dioxobicyclo[3.2.1]octane.

7-[6-carboisopropylamino-2-cis-hexenyl]-6-[3α-hydroxy-1-trans-octenyl]-3-oxo-2,4-dioxobicyclo[3.2.1] octane 7-[6-carboxy-2-cis-hexenyl]-6-[3α-pivaloyloxy-1-trans-octenyl]-3-oxo-2,4-dioxobicyclo[3.2.1]octane 7-[6-carboxbenzoxy-2-cis-hexenyl]-6-[3α-pivaloyloxy-1-trans-octenyl]-3-oxo-2,4-dioxobicyclo[3.2.1]octane.

5. A compound of formula III

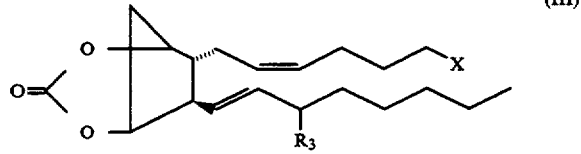

(III)

wherein hatched lines indicate α configuration, R₃ is =O, —OH or —O(CO)—R₆ wherein R₆ is a saturated or unsaturated acyclic hydrocarbon group having from 1 to about 20 carbon atoms, X is selected from the group consisting of —COOR₄, —CH₂OR₄, —CH₂N (R₄)₂ and —C(O)N(R₄)₂ wherein R₄ is hydrogen, C₁ to C₁₀ alkyl, phenyl or benzyl; or a pharmaceutically acceptable salt thereof, solid triangles are used to indicate β configuration.

6. A compound of claim 5 wherein the compound is selected from the group consisting of 7-[6-carboxy-2-cis-hexenyl-6-[3α-hydroxy- 1 -trans-octenyl]-3-oxo-2,4-dioxobicyclo[3.2.1]octane 7-[6-carbomethoxy-2-cis-hexenyl-6-[3α-hydroxy- 1-trans-octenyl]-3-oxo-2,4-dioxobicyclo[3.2.1]octane 7-[6-carbomethoxy-2-cis-hexenyl-6-[3α-pivaloyloxy-1-trans-octenyl]-3-oxo-2,4-dioxobicyclo[3.2.1]octane 7-[7-hydroxy-2-cis-heptenyl-6-[3α-hydroxy- 1 -trans-octenyl]-3-oxo-2,4-dioxobicyclo[3.2.1]octane 7-[6-carbobenzoxy-2-cis-hexenyl-6-[3α-hydroxy-1-trans-octenyl]-3-oxo-2,4-dioxobicyclo[3.2.1]octane 7-[6-carboamino-2-cis-hexenyl]-6-[3α-hydroxyl-1-trans-octenyl]-3-oxo-2,4-dioxobicyclo[3.2.1]octane 7-[6-carboisopropylamino-2-cis-hexenyl]-6-[3αhydroxy-1-trans-octenyl]-3-oxo-2,4-dioxobicyclo[3.2.1] octane 7-[6-carboxy-2-cis-hexenyl]-6-[3α-pivaloloxy-1-trans-octenyl]3-oxo-2,4-dioxobicyclo[3.2.1 ]octane 7-[6-carbobenzoxy-2-cis-hexenyl ]-6-[3α-pivaloyloxy-1-trans-octenyl]-3-oxo -2,4-dioxobicyclo[3.2.1]octane.

* * * * *

UNITED STATES PATENT AND TRADEMARK OFFICE
CERTIFICATE OF CORRECTION

PATENT NO. : 5,416,106

DATED : May 16, 1995

INVENTOR(S) : Burk et al

It is certified that error appears in the above-indentified patent and that said Letters Patent is hereby corrected as shown below:

Column 2, line 62; delete "11acetyl" and insert in place thereof -- 11-acetyl--

Column 6, line 20; delete "ct" and insert in place thereof --$\alpha$--

Column 8, line 31; delete "(3A-t-B" and insert in place thereof --(3A-t--

Column 8, line 32; delete "UTYLDIMETHYL-" and insert in place thereof --BUTYLDIMETHYL- --

Column 9, line 46; delete "3$\beta$" and insert in place thereof --3$\alpha$--

Column 9, line 64; delete "UTYLDIMETHYLSILYLOXY-" and insert in place thereof --BUTYLDIMETHYLSILYLOXY- --

Column 10, line 38; delete "et"

Column 10, line 52; delete "2$\beta$3$\alpha$" and insert in place thereof --2$\beta$, 3$\alpha$--

Column 11, line 23; delete "ehted" and insert in place thereof --eluted--

Column 12, line 9; after "Example" insert --6.--

Column 13, line 25; after "($\zeta$" delete "b"

Column 14, line 28; after "aggregatory" insert --response;--

Column 14, line 2, Table 4; after "Arachidonic" insert --Acid and ADP--

Column 14, line 3, Table 4; delete "Acid and ADP"

UNITED STATES PATENT AND TRADEMARK OFFICE
CERTIFICATE OF CORRECTION

PATENT NO. : 5,416,106
DATED : May 16, 1995
INVENTOR(S) : Burk, et al

It is certified that error appears in the above-indentified patent and that said Letters Patent is hereby corrected as shown below:

Column 15, line 6, Table 3; after "$3.3 \times 10^{-8}$" insert --Example 7--

Signed and Sealed this

Nineteenth Day of September, 1995

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,416,106
DATED : May 16, 1995
INVENTOR(S) : Burk et al

It is certified that error appears in the above-indentified patent and that said Letters Patent is hereby corrected as shown below:

Column 17, line 10; delete "ct" and insert in place thereof --$\alpha$--

Column 17, line 10; delete "Rhd 3" and insert in place thereof --$R_3$--

Column 17, line 32; delete "ct" and insert in place thereof --$\alpha$--

Column 17, line 33; after "dioxobicyclo" insert -- [3.2.1]octane--.

Column 18, line 6; delete "3oxo" and insert in place thereof --3-oxo--

Column 18, line 59; delete "3⌀hy-" and insert in place thereof --3$\alpha$-hy- --

Signed and Sealed this

First Day of October, 1996

Attest:

BRUCE LEHMAN

Attesting Officer    Commissioner of Patents and Trademarks